United States Patent [19]

Beck

[11] Patent Number: 5,304,575
[45] Date of Patent: Apr. 19, 1994

[54] USE OF BEZAFIBRATE FOR TREATING DIABETES

[75] Inventor: Walter Beck, Mannheim, Fed. Rep. of Germany

[73] Assignee: Boehringer Mannheim GmbH, Mannheim-Waldhof

[21] Appl. No.: 993,525

[22] Filed: Dec. 17, 1992

Related U.S. Application Data

[63] Continuation of Ser. No. 238,930, Aug. 31, 1988, abandoned.

[30] Foreign Application Priority Data

Sep. 1, 1987 [DE] Fed. Rep. of Germany ....... 3729209

[51] Int. Cl.$^5$ ................. A61K 31/195; A61K 31/175; A61K 49/00
[52] U.S. Cl. ..................................... 514/563; 514/592; 624/10
[58] Field of Search .................... 514/563, 592; 424/10

[56] References Cited

U.S. PATENT DOCUMENTS 4,318,923  3/1982  Hamazaki et al. .................. 514/563

Primary Examiner—Jerome Goldberg
Attorney, Agent, or Firm—Felfe & Lynch

[57] ABSTRACT

Bezafibrate is used for the treatment of normolipidaemic diabetes mellitus type II.

3 Claims, No Drawings

USE OF BEZAFIBRATE FOR TREATING DIABETES

This is a continuation of application Ser. No. 238,930 filed on Aug. 31, 1988, now abandoned.

BACKGROUND OF THE INVENTION

The present invention is concerned with the novel use of bezafibrate for the treatment of diabetes.

Bezafibrate, i.e. 2-[4-[2-(4-chlorobenzamido)ethyl]-phenoxy]-2-methylpropionic acid, is an agent known from Federal Republic of Germany Patent Specification No. 21 49 070 which is widely used for the treatment of hyperlipidaemias (hypertriglyceridae-caias and hypercholesterolaemias). Since hyperlipoproteinaemias are an especially frequently occurring accompanying metabolic disturbance in the case of diabetes mellitus and can lead to premature arteriosclerosis, in a series of studies a simultaneous treatment of hyperlipidaemic diabetics with sulphonylureas or insulin and bezafibrate has already been investigated. The decrease of the serum triglyceride and cholesterol concentration which occurs in comparison with a sole treatment with sulphonylureas or insulin thereby also leads to a significant decrease of the fasting blood sugar values. After discontinuation of the bezafibrate, all three parameters again increase. It is assumed that the strong triglyceride lowering with bezafibrate, just as in the case of appropriate diet, brings about the parallel retrogression of the glucose. An improvement of the glucose utilisation by bezafibrate is conjectured (cf. Bruneder et al., Dtsch. med. Wschr., 106, 1653-1656/1981).

SUMMARY AND DETAILED DISCLOSURE OF THE INVENTION

Surprisingly, we have now also found that in the case of type II diabetics not treated with insulin releasers, in which the triglyceride, cholesterol and HDL cholesterol values lie in the normal range so that no indication exists for the use of lipid sinkers but the blood sugar values, in spite of a strict diet, still lie significantly above the norm, by administration of bezafibrate there occurs a distinct improvement of the glucose level not only in the fasting value but also after loading with a test meal. The triglyceride and cholesterol values also sink due to the treatment but remain in the normal range.

Therefore, the present invention provides for the use of bezafibrate for the treatment of normolipidaemic diabetes mellitus type II.

The dosage to be administered is preferably from 200 to 600 mg./day. Advantageously, the daily dosage is taken together with the meal in the form of a tablet or dragee.

According to one aspect of the present invention, bezafibrate can be administered as the sole blood glucose-sinking active material. However, insofar as an insulin secretion deficiency is responsible for the diabetes, a parallel administration of insulin releasers can be necessary and, if desired, both active materials may be combined in one dosage unit. As insulin releasers, there are preferably used sulphonylureas and especially glibenclamid.

EXPERIMENTAL REPORT

Non-insulin-dependent diabetics (NIDDM), who have not been treated with other glucose level-sinking medicaments, were treated for about 1 month with a diet for the adjustment of normal blood values. Thereafter, after 10 hours fasting overnight, the fasting values (triglyceride, cholesterol, glucose, insulin) were determined in the serum and a standard meal with 500 kcal was administered. Subsequently, the insulin and blood sugar values were measured at 30 minute intervals. For 3 months thereafter, with the maintenance of the diet, a therapy was carried out with 3×200 mg./day of bezfibrate or with an appropriate placebo tablet (in a simple blind test) and again fasting values and loading values measured after a renewed test meal, the results obtained being summarised in the following Table. In the case of the loading tests, in each case the maximum value is given. In the placebo group, neither in the case of the triglyceride values nor in the case of the glucose values was a significant difference to the starting value found so that these values have been omitted.

The values given in the following Table verify that, in the case of bezafibrate therapy, the blood glucose level decreases by 10 to 20% not only in the fasting state but also with loading, although simultaneously the insulin level decreases strongly. Thus, bezafibrate also proves to be a useful agent for the treatment of such cases of normolipidaemic diabetes mellitus type II.

TABLE

|  | patient 1 | | patient 2 | | average value from 36 patients | | norm for healthy subjects |
| --- | --- | --- | --- | --- | --- | --- | --- |
|  | 0 | 3 months | 0 | 3 months | 0 | 3 months |  |
| triglycerides mmole/l. | 2.01 | 1.45 | 1.37 | 0.65 | 2.20 | 0.40 | 2.3 |
| cholesterol mmole/l. | 7.5 | 5.7 | 7.8 | 5.9 |  |  | 3.9-8.5 |
| glucose mmole/l. |  |  |  |  |  |  |  |
| fasting | 11.2 | 9.2 | 8.9 | 7.4 | 10.6 | 9.1 | 3.9-6.4 |
| loaded | 16.0 | 14.6 | 14.4 | 12.3 | 15.2 | 14.1 |  |
| insulin mU/l. |  |  |  |  |  |  |  |
| fasting | 24.9 | 13.9 | 4.0 | 3.1 |  |  |  |
| loaded | 79.0 | 56.4 | 30.5 | 25.6 |  |  |  |

What is claimed is:

1. A method for reducing the insulin level in normolipidaemic patients suffering from diabetes mellitus type II, which method comprises orally administering to said patient an effective amount of bezafibrate.

2. A method according to claim 1, in which the bezafibrate is administered at a dosage of from 200 to 600 mg. per day.

3. A method for reducing the insulin level in normolipidaemic patients suffering from diabetes mellitus type II, which method comprises orally administering to said patient, in a single dosage unit, an effective amount of bezafibrate and an effective amount of a sulphonylurea.

* * * * *